United States Patent
Hoeg et al.

(10) Patent No.: US 9,408,527 B2
(45) Date of Patent: Aug. 9, 2016

(54) SOLID STATE VARIABLE DIRECTION OF VIEW ENDOSCOPE WITH ROTATABLE WIDE-ANGLE FIELD FOR MAXIMAL IMAGE PERFORMANCE

(71) Applicant: Karl Storz Imaging, Inc., Goleta, CA (US)

(72) Inventors: Hans David Hoeg, Vancouver, WA (US); George E. Duckett, III, Castaic, CA (US)

(73) Assignee: Karl Storz Imaging, Inc., Goleta (DE)

( * ) Notice: Subject to any disclaimer, the term of this patent is extended or adjusted under 35 U.S.C. 154(b) by 72 days.

(21) Appl. No.: 13/666,534

(22) Filed: Nov. 1, 2012

(65) Prior Publication Data

US 2014/0121459 A1    May 1, 2014

(51) Int. Cl.
| | |
|---|---|
| A61B 1/06 | (2006.01) |
| G02B 26/08 | (2006.01) |
| A61B 1/00 | (2006.01) |
| A61B 1/04 | (2006.01) |
| G02B 27/64 | (2006.01) |

(52) U.S. Cl.
CPC ......... *A61B 1/00183* (2013.01); *A61B 1/00165* (2013.01); *A61B 1/00174* (2013.01); *A61B 1/00179* (2013.01); *A61B 1/04* (2013.01); *A61B 1/042* (2013.01); *A61B 1/06* (2013.01); *G02B 26/0883* (2013.01); *G02B 27/642* (2013.01)

(58) Field of Classification Search
CPC ........... A61B 1/00183; A61B 1/00096; A61B 1/00177; A61B 1/00172; A61B 1/00179; A61B 1/00181; G02B 23/24; G02B 23/243; H04N 5/2254

USPC ......... 600/173, 109, 160, 170, 137, 130, 171, 600/103, 101; 348/45, 65, 77; 356/455; 359/210.2, 210.1, 211.1; 385/117; 850/1

See application file for complete search history.

(56) References Cited

U.S. PATENT DOCUMENTS

| | | | | |
|---|---|---|---|---|
| 4,138,192 | A | * | 2/1979 | Yamasita ............... 359/726 |
| 4,655,557 | A | * | 4/1987 | Takahashi ............... 359/735 |
| 4,676,592 | A | * | 6/1987 | Nishioka et al. ............... 385/117 |
| 4,682,040 | A | * | 7/1987 | Hohki ............... G01N 21/88 |
| | | | | 250/559.07 |
| 4,772,942 | A | | 9/1988 | Tuck |
| 4,815,833 | A | * | 3/1989 | Zobel et al. ............... 359/726 |
| 4,988,172 | A | * | 1/1991 | Kanamori et al. ............... 359/654 |
| 5,023,725 | A | | 6/1991 | McCutchen |
| 5,067,019 | A | | 11/1991 | Juday et al. |
| 5,185,667 | A | | 2/1993 | Zimmermann |
| 5,313,306 | A | | 5/1994 | Kuban et al. |

(Continued)

FOREIGN PATENT DOCUMENTS

| | | |
|---|---|---|
| EP | 1686410 A1 | 8/2006 |
| WO | 0139657 A1 | 6/2001 |

OTHER PUBLICATIONS

European Search Report Application No. EP 13 19 0669 Completed: Jan. 27, 2014; Mailing Date: Feb. 6, 2014 6 pages.

*Primary Examiner* — Matthew J Kasztejna
*Assistant Examiner* — Aaron B Fairchild
(74) *Attorney, Agent, or Firm* — Whitmyer IP Group LLC (57) ABSTRACT

An endoscope and endoscopic surgical system for improving the image resolution/performance of a solid state variable direction of view endoscope. The endoscope and endoscopic surgical system has an optical rotator element that optically rotates the entire wide-angle field so as to make any portion of the wide-angle field visible to an image sensor.

54 Claims, 7 Drawing Sheets

(56) References Cited

U.S. PATENT DOCUMENTS

| | | | |
|---|---|---|---|
| 5,359,363 A | 10/1994 | Kuban et al. | |
| 5,384,588 A | 1/1995 | Martin et al. | |
| 5,391,144 A * | 2/1995 | Sakurai et al. | 604/22 |
| 5,588,948 A * | 12/1996 | Takahashi et al. | 600/111 |
| 5,621,830 A * | 4/1997 | Lucey et al. | 385/25 |
| 5,630,782 A | 5/1997 | Adair | |
| 5,689,365 A * | 11/1997 | Takahashi | 359/362 |
| 5,720,706 A * | 2/1998 | Takahashi et al. | 600/111 |
| 5,743,846 A * | 4/1998 | Takahashi et al. | 600/166 |
| 5,800,341 A | 9/1998 | McKenna et al. | |
| 5,836,869 A * | 11/1998 | Kudo et al. | 600/173 |
| 5,891,015 A * | 4/1999 | Strahle | 600/160 |
| 5,954,634 A * | 9/1999 | Igarashi | 600/109 |
| 6,002,430 A | 12/1999 | McCall et al. | |
| 6,215,519 B1 | 4/2001 | Nayar et al. | |
| 6,306,082 B1 * | 10/2001 | Takahashi et al. | 600/173 |
| 6,371,909 B1 * | 4/2002 | Hoeg et al. | 600/173 |
| 6,449,103 B1 | 9/2002 | Charles | |
| 6,464,631 B1 * | 10/2002 | Girke et al. | 600/109 |
| 6,471,637 B1 * | 10/2002 | Green et al. | 600/109 |
| 6,500,115 B2 * | 12/2002 | Krattiger et al. | 600/173 |
| 6,501,551 B1 * | 12/2002 | Tearney et al. | 356/477 |
| 6,606,113 B2 * | 8/2003 | Nakamura | 348/45 |
| 6,626,828 B2 * | 9/2003 | Dohi et al. | 600/173 |
| 6,648,817 B2 * | 11/2003 | Schara et al. | 600/173 |
| 6,695,774 B2 * | 2/2004 | Hale et al. | 600/173 |
| 6,859,229 B1 * | 2/2005 | Suda | H01L 27/14627 348/273 |
| 6,902,528 B1 | 6/2005 | Garibaldi et al. | |
| 6,930,705 B2 * | 8/2005 | Tanaka | 348/45 |
| 6,936,003 B2 | 8/2005 | Iddan | |
| 6,976,956 B2 * | 12/2005 | Takahashi et al. | 600/166 |
| 7,037,258 B2 * | 5/2006 | Chatenever et al. | 600/109 |
| 7,101,334 B2 * | 9/2006 | Takahashi | 600/166 |
| 7,161,741 B1 * | 1/2007 | Schaack | 359/676 |
| 7,211,042 B2 * | 5/2007 | Chatenever | 600/117 |
| 7,261,687 B2 * | 8/2007 | Yang | 600/173 |
| 7,355,625 B1 | 4/2008 | Mochida et al. | |
| 7,382,399 B1 | 6/2008 | McCall et al. | |
| 7,544,162 B2 * | 6/2009 | Ohkubo | 600/173 |
| 7,554,572 B2 * | 6/2009 | Takahashi | 348/65 |
| 7,559,890 B2 | 7/2009 | Wallace et al. | |
| 7,714,936 B1 | 5/2010 | Martin et al. | |
| 7,744,528 B2 | 6/2010 | Wallace et al. | |
| 7,833,152 B2 * | 11/2010 | Chatenever et al. | 600/117 |
| 7,896,803 B2 * | 3/2011 | Schara et al. | 600/173 |
| 8,360,964 B2 * | 1/2013 | Ertas | 600/166 |
| 8,634,124 B2 * | 1/2014 | Yoshikawa | 359/211.2 |
| 2001/0012053 A1 * | 8/2001 | Nakamura | 348/45 |
| 2002/0022767 A1 * | 2/2002 | Dohi et al. | 600/173 |
| 2002/0082476 A1 * | 6/2002 | Takahashi et al. | 600/173 |
| 2002/0085272 A1 * | 7/2002 | Tomioka et al. | 359/362 |
| 2002/0161280 A1 * | 10/2002 | Chatenever et al. | 600/112 |
| 2003/0083551 A1 * | 5/2003 | Takahashi | 600/166 |
| 2003/0092966 A1 * | 5/2003 | Schara et al. | 600/173 |
| 2003/0097044 A1 * | 5/2003 | Rovegno | 600/170 |
| 2004/0181148 A1 * | 9/2004 | Uchiyama et al. | 600/425 |
| 2005/0020883 A1 * | 1/2005 | Chatenever et al. | 600/173 |
| 2005/0027167 A1 * | 2/2005 | Chatenever et al. | 600/173 |
| 2005/0154260 A1 * | 7/2005 | Schara et al. | 600/117 |
| 2005/0177026 A1 * | 8/2005 | Hoeg et al. | 600/173 |
| 2005/0264672 A1 * | 12/2005 | Takahashi | 348/335 |
| 2006/0206003 A1 * | 9/2006 | Hoeg et al. | 600/117 |
| 2006/0206006 A1 * | 9/2006 | Schara et al. | 600/173 |
| 2006/0252995 A1 * | 11/2006 | Hoeg et al. | 600/173 |
| 2006/0256450 A1 * | 11/2006 | Tesar et al. | 359/727 |
| 2007/0066871 A1 * | 3/2007 | Yang et al. | 600/173 |
| 2007/0191682 A1 * | 8/2007 | Rolland et al. | 600/173 |
| 2008/0021282 A1 * | 1/2008 | Hoeg et al. | 600/173 |
| 2008/0091064 A1 | 4/2008 | Laser | |
| 2009/0231983 A1 * | 9/2009 | Takahashi | 369/112.04 |
| 2009/0318758 A1 | 12/2009 | Farr et al. | |
| 2010/0010301 A1 * | 1/2010 | Hale et al. | 600/109 |
| 2010/0152539 A1 | 6/2010 | Ghabrial et al. | |
| 2010/0195007 A1 * | 8/2010 | Takahashi | 349/16 |
| 2011/0199531 A1 * | 8/2011 | Yoshikawa | 348/340 |
| 2011/0288374 A1 * | 11/2011 | Hadani et al. | 600/113 |
| 2012/0116158 A1 * | 5/2012 | Hale et al. | 600/109 |
| 2013/0057828 A1 * | 3/2013 | de Smet | 351/207 |
| 2013/0204084 A1 * | 8/2013 | Hale et al. | 600/109 |

\* cited by examiner

SOLID STATE VARIABLE DIRECTION OF VIEW ENDOSCOPE WITH ROTATABLE WIDE-ANGLE FIELD FOR MAXIMAL IMAGE PERFORMANCE

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

FIELD OF THE INVENTION

The invention is directed to an endoscope and endoscopic surgical system having an image sensor and optical rotator that facilitate capture of a wide-angle viewing field, where the optical rotator is rotatable to make various portions of the wide-angle viewing field detectable by the image sensor.

BACKGROUND OF THE INVENTION

Variable direction of view endoscopes allow a user to change the endoscopic viewing direction without having to change the position of the endoscope itself. Such endoscopes are useful when the user wants to see structures which are beside or behind the tip of the endoscope, but cannot easily move the endoscope shaft because of anatomical constraints or constraints imposed by other surgical instruments in the operative field.

Solid state variable direction of view endoscopes are robust and less expensive to make than typical surgical endoscopes. Solid state variable direction of view endoscopes provide surgeons with the ability to move the displayed field of view within a larger global wide-angle field. This has the advantage of maintaining the field of view of traditional endoscopy while providing the user with the ability to effectively change the viewing direction of the endoscope, which is desirable in many cases.

The ability to maintain the field of view while providing the user with the ability to effectively change the viewing direction of the endoscope (mode of operation) is preferred to wide-angle endoscopy because surgeons have difficulty with fields which are too wide. Surgical work such as cutting and suturing typically happens over a narrow area and a wide viewing field presented on a surgical display all at once makes particular regions of interest too small when displayed on a fixed size screen. Furthermore, wide viewing fields suffer from distortion, and it is not psychologically natural for humans to relate to viewing wide-angle views such as those produced by broad fisheye type lenses, because humans have a narrow field of visual acuity.

Variable direction of view endoscopes are described in co-pending U.S. patent application Ser. No. 12/169,290 entitled "Solid State Variable Direction Of View Endoscope" filed on Jul. 8, 2008 and U.S. patent application Ser. No. 13/354,801 entitled "Wide Angle Flexible Endoscope" filed on Jan. 20, 2012. The contents of U.S. patent application Ser. Nos. 13/354,801 and 12/169,290 are hereby incorporated into this application by reference in their entirety. Additionally, variable direction of view endoscopes using deployable endoscope technology are described in U.S. patent application Ser. No. 13/572,149 entitled "Deployable Imaging System Equipped With Solid State Imager", filed on Aug. 10, 2012. The contents of U.S. patent application Ser. No. 13/572,149 application is hereby incorporated into this application by reference in its entirety.

Endoscopic surgical systems using variable direction of view endoscopes are desirable because such systems afford surgeons greater flexibility in their procedural approach. Known endoscopic surgical systems include: U.S. Pat. No. 7,355,625 (Mochida et al); U.S. Pat. No. 6,936,003 Iddan; U.S. Pat. No. 6,902,528 Garibaldi et al.; U.S. Pat. No. 5,630,782 Adair; U.S. Patent Publication No. 2010/0152539 A1 Ghabrial et al.; U.S. Patent Publication No. 2009/0318758 A1 Farr et al.; U.S. Pat. No. 7,744,528 (Wallace et al.); U.S. Pat. No. 7,714,936 (Martin et al.); U.S. Pat. No. 7,559,890 (Wallace et al.); U.S. Pat. No. 7,382,399 (Mccall et al.); U.S. Pat. No. 6,449,103 (Charles); U.S. Pat. No. 6,215,519 (Nayar et al.); U.S. Pat. No. 6,002,430 (McCall et al.); U.S. Pat. No. 5,954,634 (Igarashi); U.S. Pat. No. 5,800,341 (McKenna et al.); U.S. Pat. No. 5,384,588 (Martin et al.); U.S. Pat. No. 5,359,363 (Kuban et al.); U.S. Pat. No. 5,313,306 (Kuban et al.); U.S. Pat. No. 5,185,667 (Zimmermann); U.S. Pat. No. 5,067,019 (Juday et al.); U.S. Pat. No. 5,023,725 (McCutchen); and U.S. Pat. No. 4,772,942 (Tuck).

Known commercial endoscopic systems include the Olympus IMAGETRAC® system, which has a proximal camera/image sensor mounted on a stage/gantry which allow the camera to move in 8 different directions. However, the IMAGETRAC® system has poor ergonomics, is expensive and complicated to make, is fragile, and difficult to sterilize.

Furthermore, prior art endoscopic surgical systems suffer from various deficiencies and disadvantages. A main disadvantage with these systems is image performance. In solid state variable direction of view endoscopy, the image sensor with a fixed amount of pixels must capture the entire widefield and then present to the user only a portion of the field at a time. In traditional endoscopy this same number of pixels is dedicated to a much smaller field/area, thus providing better image resolution/performance than compared to typical solid state variable direction of view endoscopes.

Thus, it is desirable to provide a solid state variable direction of view endoscope that addresses these image performance issue and allows solid state variable direction of view endoscopes to have comparable image resolution/performance to traditional endoscopic systems.

SUMMARY OF THE INVENTION

Accordingly, it is an object of the invention to provide a solid state variable direction of view endoscope that addresses and solves the image performance disadvantage typically associated with solid state variable direction of view endoscopes. It is another object of the invention to provide a solid state variable direction of view endoscope and endoscopic surgical system that has comparable image resolution/performance to traditional endoscopic systems.

These objects of the invention are achieved by providing an endoscope comprising: a body having a distal end, a proximal end, and a longitudinal axis, a wide-angle objective lens disposed in the distal end of the body for capturing light of a wide viewing field, an image sensor disposed in the body for detecting the light captured by the wide-angle objective lens and forming one or more images of the wide viewing field, and an optical rotator interposed between the objective lens and the image sensor, wherein the optical rotator is rotated such that any portion of the wide viewing field detected by the image sensor is a sensor view.

In certain embodiments, the body of the endoscope is wider at the proximal end of the body than at the distal end of the body. In certain embodiments, the body of the endoscope may be a shaft. In certain embodiments, the body of the endoscope may be a combination of a shaft/handle, where the shaft/handle is wider at the proximal end of the shaft/handle than at the distal end of the shaft/handle. In certain embodiments, the shaft/handle may be tapered.

In certain embodiments, the wide-angle objective lens may transmit the captured light of the wide viewing field to the optical rotator. The optical rotator may then transmit the captured light of the wide viewing field to the image sensor for detection. In certain embodiments, the sensor is offset from an optical axis such that only some of the captured light is detected by the sensor. In certain embodiments, only some of the captured light is detected by the sensor at any given moment.

In certain embodiments, a relay lens system may be interposed between the optical rotator and the image sensor. The optical rotator may transmit the captured light of the wide viewing field to the relay lens system; therefore, the relay lens system may re-transmit the captured light to the image sensor for detection.

In certain embodiments, a relay lens system may be interposed between the objective lens and the optical rotator. The objective lens may transmit the captured light of the wide viewing field to the relay lens system; therefore, the relay lens system may transmit the captured light to the optical rotator. The optical rotator may transmit the captured light of the wide viewing field images to the image sensor for detection. In certain embodiments, the sensor is offset from an optical axis such that only some of the captured light is detected by the sensor.

In certain embodiments, the endoscope may further comprise an image rotator, which may rotate the orientation of the sensor view. The image rotator may be in communication with a processor for manipulating image data received from the image sensor. As is commonly known in the art, various types of processors are capable of manipulating both still and video image data for electronic image zoom, flip, invert, rotation, and the like. In certain embodiments, the image rotator may be in communication with a processor, wherein the processor changes the orientation of the sensor view in accordance with a user input or with a predetermined algorithm.

In certain embodiments, the optical rotator may be a be rotational prism, such as a Dove, or a reversion or "K" prism. A Dove-prism is a type of reflective prism used to rotate an image. Dove prisms are shaped from a truncated right-angle prism. A beam of light entering one of the sloped faces of the prism undergoes total internal reflection from the inside of the longest (bottom) face and emerges from the opposite sloped face. Images passing through a Dove prism are flipped, and because only one reflection takes place, the image is inverted but not laterally transposed. A K-prism is a triangular prism with a triangular base and rectangular sides. In certain embodiments, other types of known prisms, such as Delta or Pechan prisms, may be used in the endoscope.

In certain embodiments, the endoscope may further comprise an actuator for rotating the optical rotator. The actuator may be a hydraulic, mechanical, or an electrical/electronic actuator; and, may utilize pins, gears, magnets, or other type of elements, that can initiate and control the rotation of the optical rotator.

In certain embodiments, the endoscope may comprise a controller for actuating the optical rotator in accordance with an input signal from an input device. The controller may be processor and/or microprocessor based for precisely regulating the position of the actuator. The controller may contain circuitry necessary to interpret and execute instructions from an input device. As a result of interpreting and executing the instructions, the controller may output corresponding instructions and/or signals to initiate and regulate the actuator position.

In certain embodiments, the endoscope may further comprise an input device for selecting a region of interest within the wide angle viewing field, the region being not larger than the sensor view. The input device may be selected from group a consisting of a knob, button, joystick, touchpad, touchscreen, voice control, gesture detection, foot pedal and combinations thereof. The input device is used for selecting and/or controlling which portion of the wide viewing field is the sensor view. The input device can be used by a user or can be an automatic element.

In certain embodiments, the endoscope may further comprise an illumination system. The illumination system may provide light to the wide-viewing field. The illumination system may be made of one or more light emitting diodes (LEDs). The illumination system may further include other known methods for providing light to a viewing field.

In certain embodiments, the endoscope is attached to a display, the display able to display the sensor view.

In certain embodiments, the endoscope may further comprise an input facility, the input facility being part of the input device or comprising a graphical user interface. The input facility may be a computer, a cloud computing module, and/or a facility that allows the images to be processed and viewed. In certain embodiments, the display may be part of the input facility.

In certain embodiments, the input facility may involve moving the region of interest on the image sensor so as to display different portions of the wide viewing field. The moving of the region of interest may comprise calculations by a processor to relate the specified trajectory of the region of interest to the physical parameters of the mechanics of the endoscope. The calculations may comprise mathematical parameterization based on polar, Euclidean, or other appropriate coordinate systems. The moving of the region of interest may be done within any coordinate system.

In certain embodiments, the input facility may involve selecting the region of interest so as to display different portions of the wide viewing field. In certain embodiments the selecting is done automatically and without human interaction with the input device or the input facility.

In certain embodiments, the wide-angle lens may continuously capture light of a wide viewing field. By continuously capturing images of a wide viewing field, a surgeon may receive continuous real time data of the wide viewing field, region of interest and sensor view.

In certain embodiments, the endoscope body may have a diameter of less than 3 mm. In certain embodiments, the endoscope body may be a percutaneous shaft, so that the endoscope may be used for percutaneous surgery. In other embodiments, the endoscope may be deployable and has a coupling mechanism to connect with various working elements. In certain embodiments, the endoscope body may be ridged, semi-ridged, flexible or a combination thereof.

In certain embodiments, the endoscope body may include a handle affixed to the proximal end of the body, where the image sensor may be disposed in the handle.

In certain embodiments, the objective lens and the optical rotator may further comprise an optical axis, wherein the optical axis is substantially parallel to the longitudinal axis. In certain embodiments, the optical axis is included in the sensor view.

In certain embodiments, the endoscope may include an illumination system providing light to at least a portion of the wide viewing field.

In certain embodiments, the image sensor continuously captures the light provided by the wide-angle objective lens. In certain embodiments, the image sensor captures only a partial amount of the light provided by the wide-angle objective lens.

Other objects of the invention are achieved by providing an endoscopic surgical system comprising: an endoscope having a body having a proximal end and a distal end, a wide-angle objective lens disposed in the distal end of the body for capturing light of a wide viewing field, an image sensor disposed at the body for detecting the light captured by the wide-angle object lens and forming one or more images of the wide viewing field, a relay lens system interposed between the objective lens and the optical rotator, the relay lens system transmitting the captured light of the wide viewing field, and an optical rotator interposed between the relay lens system and the image sensor, wherein the optical rotator is rotated such that any portion of the wide viewing field detected by the image sensor is a sensor view; and an input device, wherein the input device allows a user to select a portion of the sensor view corresponding to a region of interest in the wide viewing field; and a display for presenting to the user the selected portion of the sensor view corresponding to the region of interest in the wide viewing field.

In certain embodiments, the body of the endoscope is wider than the proximal end of the body than at the distal end of the body. In certain embodiments, the body of the endoscope may be a shaft. In certain embodiments, the body of the endoscope may be a combination of a shaft/handle, where the shaft/handle is wider than the proximal end of the shaft/handle than at the distal end of the shaft/handle.

In certain embodiments, the endoscope further comprises a solid-state image rotator. In certain embodiments, the solid-state image rotator may be in communication with a processor for manipulating image data received from the image sensor. As is commonly known in the art, various types of processors are capable of manipulating both still and video image data for electronic image zoom, flip, invert, rotation, and the like. In certain embodiments, the image rotator may be in communication with a processor, wherein the processor changes the orientation of the sensor view in accordance with a user input or with a predetermined algorithm.

In certain embodiments, the optical rotator of the endoscope may be selected from a group consisting of: Dove-prisms, reversion or "K" prisms, delta prisms, and Pechan prisms.

In certain embodiments, the endoscopic surgical system may further comprise an actuator for rotating the optical rotator of the endoscope. In certain embodiments, the actuator may be a hydraulic or a mechanical actuator.

In certain embodiments, the endoscope may further comprise a controller for actuating the optical rotator in accordance with an input signal from the input device.

In certain embodiments, the input device allows a user to select a portion of the field of view corresponding to a region of interest on the image sensor. The input device may be a knob, button, joystick, touchpad, touchscreen, voice, gesture detection, foot pedal and combinations thereof.

In certain embodiments, the objective lens of the endoscope is a wide-angle lens. In certain embodiments, the endoscopic surgical system may further comprise an image rotator. The image rotator may be a solid state/electronic image rotator for electronically rotating/changing the orientation of the sensor view.

In certain embodiments, the endoscopic surgical system may further comprise an illumination system. The illumination system may provide light to the wide viewing field. The illumination system may be made of one or more light emitting diodes (LEDs). The illumination system may further include other known methods for providing light to a viewing field.

In certain embodiments, the endoscope body includes a handle affixed to the proximal end of the body, the image sensor being disposed in the handle.

In certain embodiments, the objective lens, the relay lens, and the optical rotator further comprise an optical axis, wherein the optical axis is substantially parallel to the longitudinal axis. In certain embodiments, the optical axis is included in the sensor view.

In certain embodiments, the image sensor continuously captures the light provided by the wide-angle objective lens. In certain embodiments, the image sensor captures only a partial amount of the light provided by the wide-angle objective lens.

Other objects of the invention are achieved by providing an endoscope comprising: a body having a longitudinal axis, a proximal end and a distal end; a wide-angle objective lens disposed in the distal end of the body, the wide-angle objective lens being able to collect light from a wide viewing field; an illumination system for providing light to said wide viewing field; an electronic image sensor disposed in the body; and an optical rotator interposed between the wide-angle objective lens and the electronic image sensor for rotating the wide viewing field such that any portion of said wide viewing field detected by the electronic image sensor is the sensor view.

In certain embodiments, the body of the endoscope is wider than the proximal end of the body than at the distal end of the body. In certain embodiments, the body of the endoscope may be a shaft. In certain embodiments, the body of the endoscope may be a combination of a shaft/handle, where the shaft/handle is wider than the proximal end of the shaft/handle than at the distal end of the shaft/handle.

In certain embodiments, the endoscope is coupled to a display and to an input device to form an endoscopic surgical system.

In certain embodiments, the endoscope further comprises an optical image transmission system interposed between the wide-angle objective lens and the optical rotator, the optical image transmission system receiving the light captured by the wide-angle objective lens, wherein the captured light is received by the optical rotator, wherein the optical rotator transmits the captured light of the wide viewing field to the electronic image sensor for detection at any given time, and wherein the sensor is offset from an optical axis that is substantially parallel to the longitudinal axis of the body, such that only some of the captured light is detected by the sensor.

In certain embodiments, a lens that provides for f-sin(theta) distortion is incorporated within the transmission system of an endoscope. In certain embodiments, the wide angle lens system includes a lens that provides for f-sin(theta) distortion.

In certain embodiments, the distortion of the endoscope transmission system is of the f-sin(theta) type. In other embodiments, the distortion of the endoscope transmission system is of the f-theta type.

In certain embodiments, the endoscope further comprises an optical image transmission system interposed between the objective lens and the electronic image sensor, the optical rotator receiving the captured light from the wide-angle objective lens and the optical rotator transmitting the captured light of the wide viewing field to the optical image transmission system for detection by the electronic image sensor at any given time.

In certain embodiments, the endoscope may be coupled to a display and an input device to form an endoscopic surgical system. In certain embodiments, the optical rotator is a rotational prism selected from the group consisting of: Dove-prisms, reversion or "K"-prisms, delta prisms and Pechan prisms. In other embodiments, other types of optical rotator elements may be used.

In certain embodiments, the optical image transmission system is a relay lens system. In certain embodiments, the optical image transmission system is a coherent image fiber bundle.

In certain embodiments, the endoscope may further comprise a solid state image rotator for electronically rotating the orientation of said sensor view. In certain embodiments, the solid-state image rotator may be in communication with a processor for manipulating image data received from the image sensor. As is commonly known in the art, various types of processors are capable of manipulating both still and video image data for electronic image zoom, flip, invert, rotation, and the like. In certain embodiments, the image rotator may be in communication with a processor, wherein the processor changes the orientation of the sensor view in accordance with a user input or with a predetermined algorithm. In certain embodiments, the endoscope may further comprise an actuator for rotating the optical rotator.

In certain embodiments, the input device is selected from a group consisting of a knob, button, joystick, touchpad, touchscreen, foot pedal, gesture detection, voice control and combinations thereof.

In certain embodiments, the endoscope further comprises an input facility, wherein the input facility is part of the input device. In certain embodiments, the input facility is a graphical user interface or is automatic.

In certain embodiments, the input facility involves moving the region of interest within the wide viewing field so as to select different portions of the field.

In certain embodiments, the endoscope may further comprise a controller for actuating the optical rotator in accordance with an input signal from the input device. In certain embodiments, the actuating of the optical rotator may be automatic, where the portion of the wide viewing field, and/or the region of interest within the wide view field, may be automatically selected from a plurality of viewing angles preset by a user. In certain embodiments, the actuating of the optical rotator may be automatic, where the portion of the wide viewing field, and/or the region of interest within the wide view field, may be automatically selected from standard viewing angles typically used within endoscopy, including, but not limited to, 0, 30, 45, 70, or 90 degrees.

In certain embodiments, the endoscope body has a diameter of less than 3 mm. In certain embodiments, the endoscope body is rigid, semi-rigid, flexible or a combination thereof. In certain embodiments, the body is a percutaneous shaft. In certain embodiments, the endoscope body has a handle affixed to the proximal end of the body, the image sensor being disposed in the handle.

In certain embodiments, the objective lens, the relay lens, and the optical rotator further comprise an optical axis, wherein the optical axis is substantially parallel to the longitudinal axis. In certain embodiments, the optical axis is included in the sensor view.

In certain embodiments, the image sensor continuously captures the light provided by the wide-angle objective lens.

In certain embodiments, the image sensor captures only a partial amount of the light provided by the wide-angle objective lens.

Other objects of the invention are achieved by providing an endoscope comprising a body having a proximal end and a distal end; an objective lens disposed in the distal end of the body; an image sensor disposed at the proximal end of the body; a relay lens system interposed between the objective lens and the image sensor; and an optical rotator interposed between the objective lens and the image sensor.

Other objects of the invention are achieved by providing an endoscope having: a body having a proximal end and a distal end, an objective lens disposed in the distal end of the body, an image sensor disposed at the proximal end of the body, a relay lens system interposed between the objective lens and the image sensor, and an optical rotator interposed between the objective lens and the image sensor; an input device; and a display.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

BRIEF DESCRIPTION OF THE DRAWINGS

FIG. 4a depicts an inverted distal "on end" view of the endoscope of FIG. 3a;

FIG. 4b depicts an inverted cross sectional side view of the endoscope of FIG. 3b, where the optical rotator is inverted;

FIG. 5a depicts a rotated distal "on end" view of the endoscope of FIG. 3a;

DETAILED DESCRIPTION OF THE INVENTION

The following detailed description illustrates the invention by way of example, not by way of limitation of the principles of the invention. This description will enable one skilled in the art to make and use the invention, and describes several embodiments, adaptations, variations, alternatives and uses of the invention, including what is presently believed to be the best mode of carrying out the invention.

The present invention addresses the image performance disadvantage of solid state variable direction of view endoscopes by dedicating the available image sensor pixels to only a portion of the wideangle field captured by the optical objective system of the endoscope and then optically rotating the entire wide-angle field so as to make any portion of the wide-angle field "visible" to the sensor as desired.

This optical rotation is best achieved with an optical rotator element such a Dove- or a K-prism. It is also possible to rotate the image sensor itself. The result of this technique is an image resolution comparable (in some modes equal) to traditional endoscopy.

Figure 1:
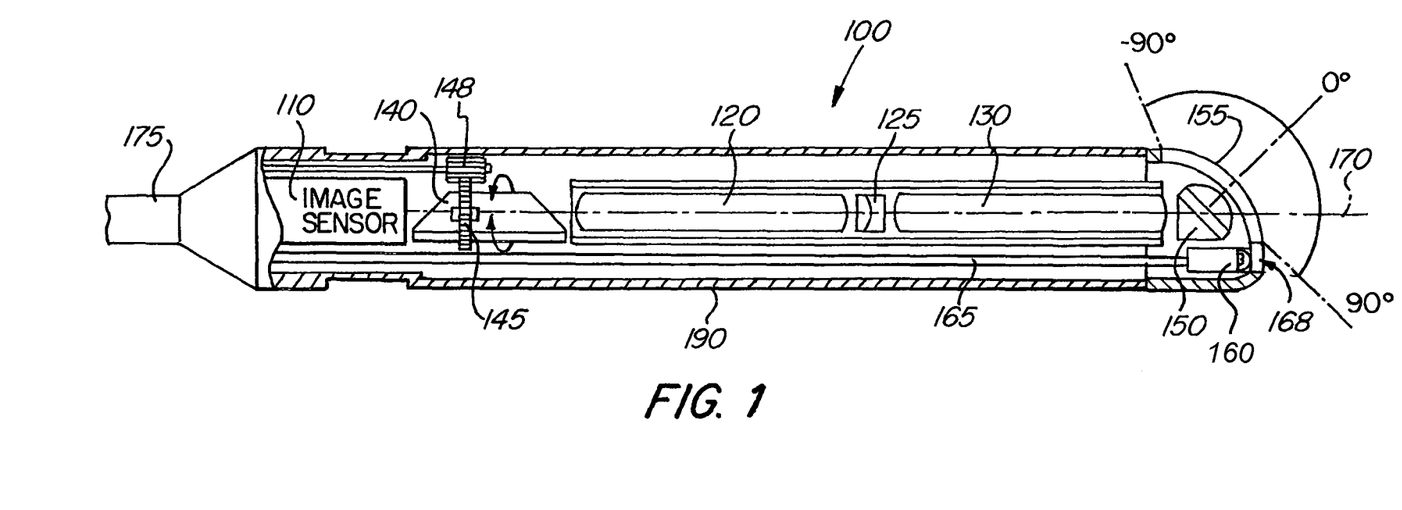
FIG. 1 is a side view of an endoscope of an embodiment of the invention.

FIG. 1 depicts an exemplary endoscope 100 of an embodiment of the invention. Endoscope 100 has a body 190 with a wide angle lens 150 incorporated within the distal end of the body 190. Endoscope 100 has a longitudinal axis 170 extending from the proximal end to the distal end of the endoscope 100.

Lens window 155 is shown at the distal end of the body 190. Lens window 155 is fully sealable. Endoscope 100 may be sterilized in an autoclave or other sterilization system.

Optical rotator 140 is also shown as a Dove-prism. Actuator 145 is shown being able to rotate the optical rotator. Controller 148 is shown being able to control the actuation of the actuator in accordance with an input signal from said input device. Actuator 145 is shown as a gear and controller 148 as an element that engages the gear. Other types of actuators and controllers may be used in various embodiments of the invention.

FIG. 1 also shows relay lens system 120/125/130. The relay lens system 120/125/130 may be made of singlets and doublets and may use the relay system described in co-pending U.S. patent application Ser. No. 13/429,853 entitled "Compensated Relays For Reducing Number of Elements in Rod Lens Endoscopes" filed Mar. 26, 2012. The contents of this application is hereby incorporated by reference into this application in its entirety.

FIG. 1 also shows illumination system 160 disposed in the distal end of endoscope 100. Illumination system 160 may be composed of one or more light emitting diodes or other illumination elements known in the art. Wiring 165 provides power to illumination system 160. Lens window 168 is shown at the distal end of the body 190 and is fully sealable.

FIG. 1 also shows image sensor 110 incorporated in the proximal portion of endoscope 100. The proximal portion of the endoscope has a power cord 175 that provides power for the elements of the endoscope.

In certain embodiments, the endoscope may have a working channel in the endoscope body that can allow working elements to pass through the endoscope.

In certain embodiments, the endoscope body may be tapered. In certain embodiments, endoscope body 190 may be a shaft and/or shaft/handle assembly.

Figure 2:
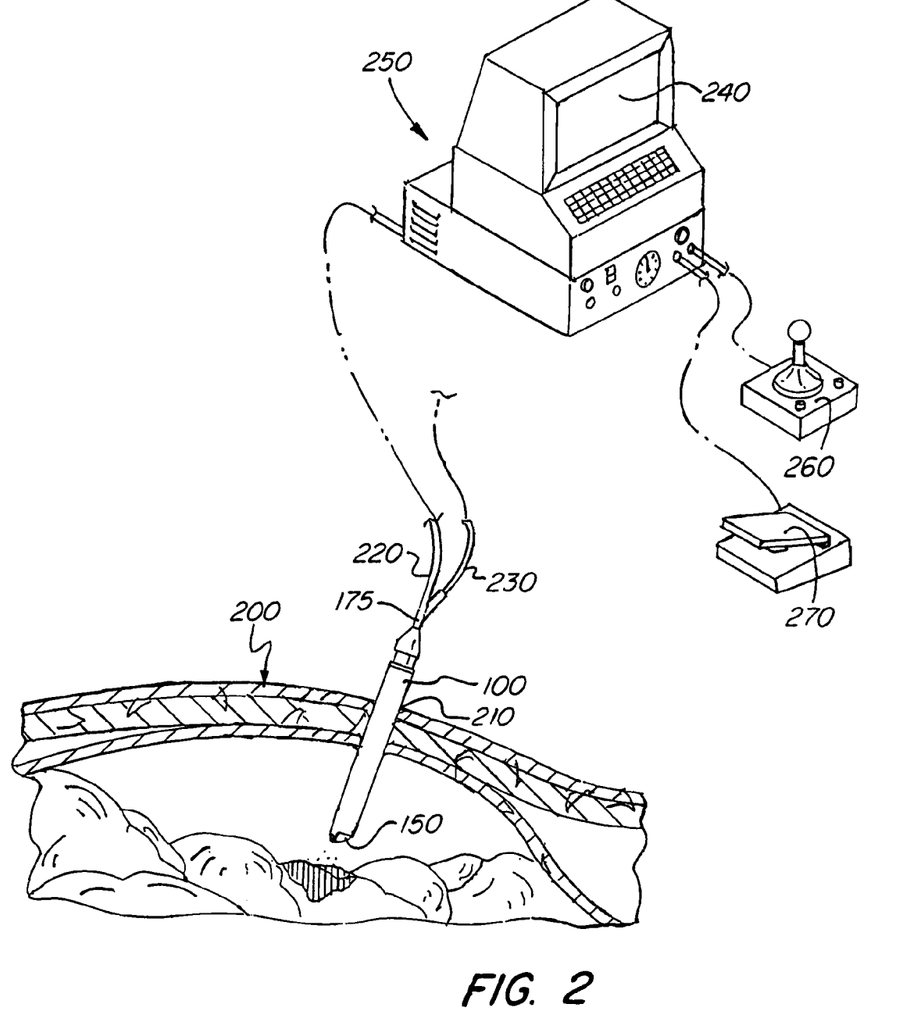
FIG. 2 is a perspective view of an endoscope of FIG. 1 connected to a display and input device of an embodiment of the present invention.

FIG. 2 shows a view of the endoscope of an embodiment of the invention where the endoscope 100 is shown being used through the skin 200 of a patient. In FIG. 2, endoscope 100 is shown being able to pass through hole 210, which preferably has a diameter of less than 3 mm. Endoscope 100 is shown connected via cable 220 to a computer 250, which is controlled by keypad 270 or joystick 260. The keypad 270 and/or joystick 260 control the solid state variable direction of views of the endoscope 100. The keypad 270, and joystick 260 are examples of the input device. Other input devices include a knob, foot pedal, touchpad, and touchscreen, as well as gesture detection and voice control input devices.

The computer 250 is an example of an input facility. The input facility 250 may incorporate display 240. However, the display 240 may be separate and distinct from input facility 250 in various embodiments of the invention. FIG. 2 also shows cable 230, as multiple power cords may be used with endoscope 100.

Figure 3:
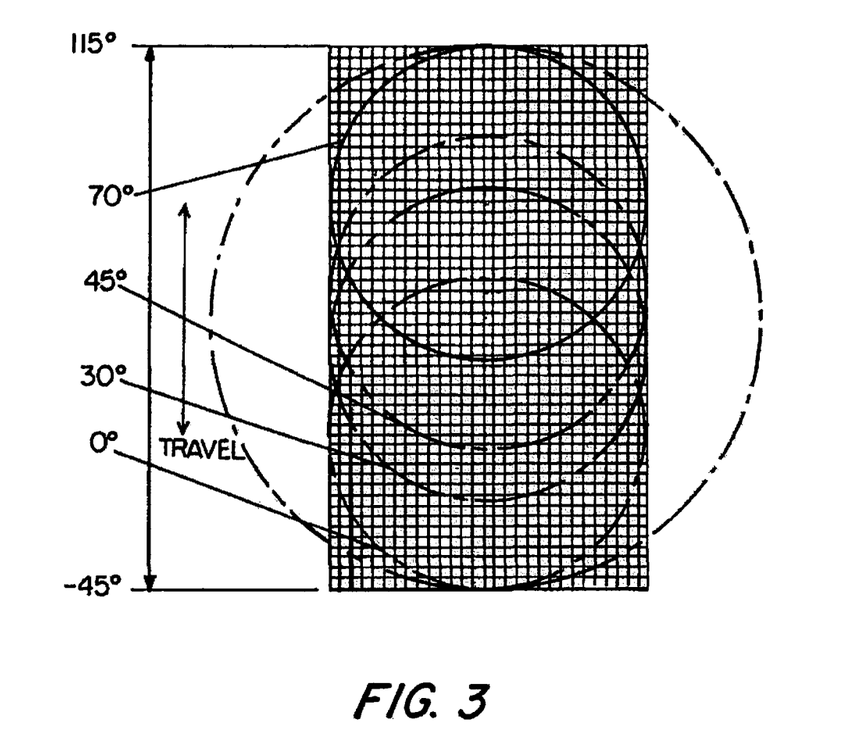
FIG. 3 is a depiction of the region of interest of image sensor of the endoscope of the present invention relative to the endoscopic field of view.
Figures 3A, 3B:
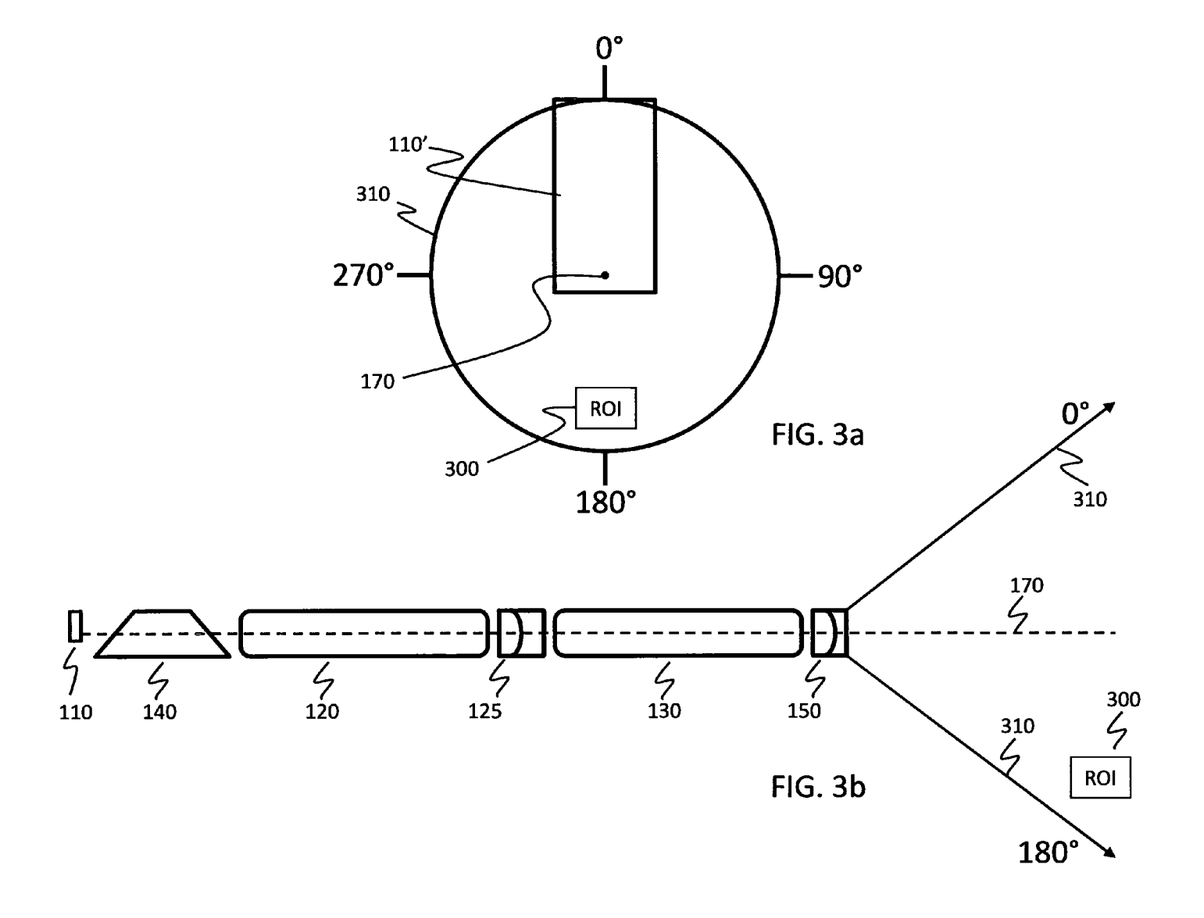
FIG. 3a depicts a distal "on end" view of the endoscope.
FIG. 3b depicts a cross sectional side view of the endoscope.
Figures 4A, 4B:
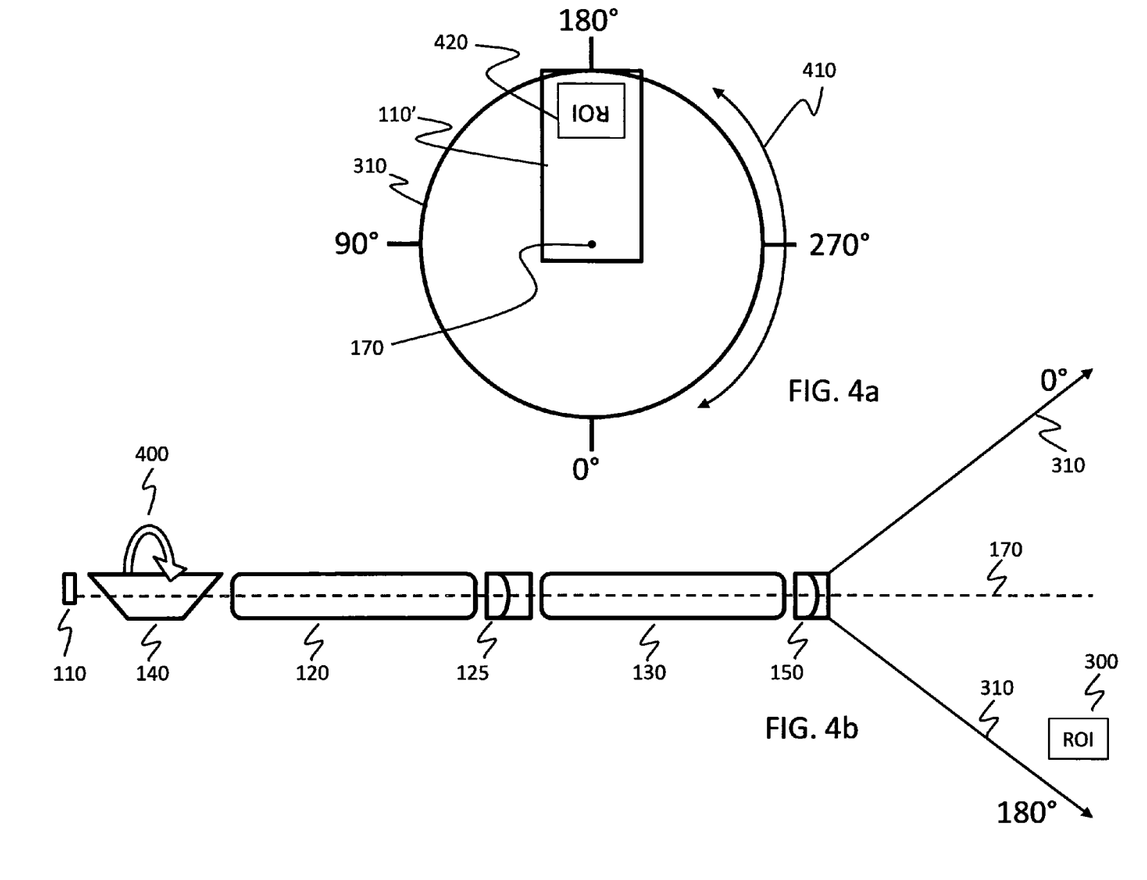
Figure 5A:
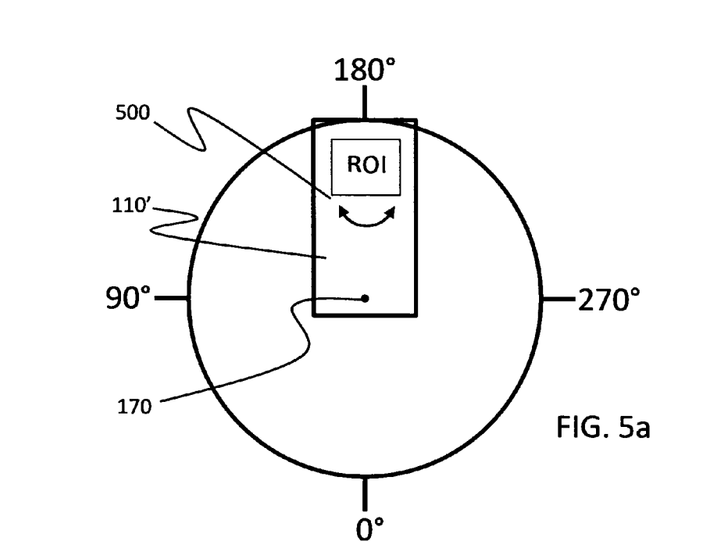
Figure 5B:
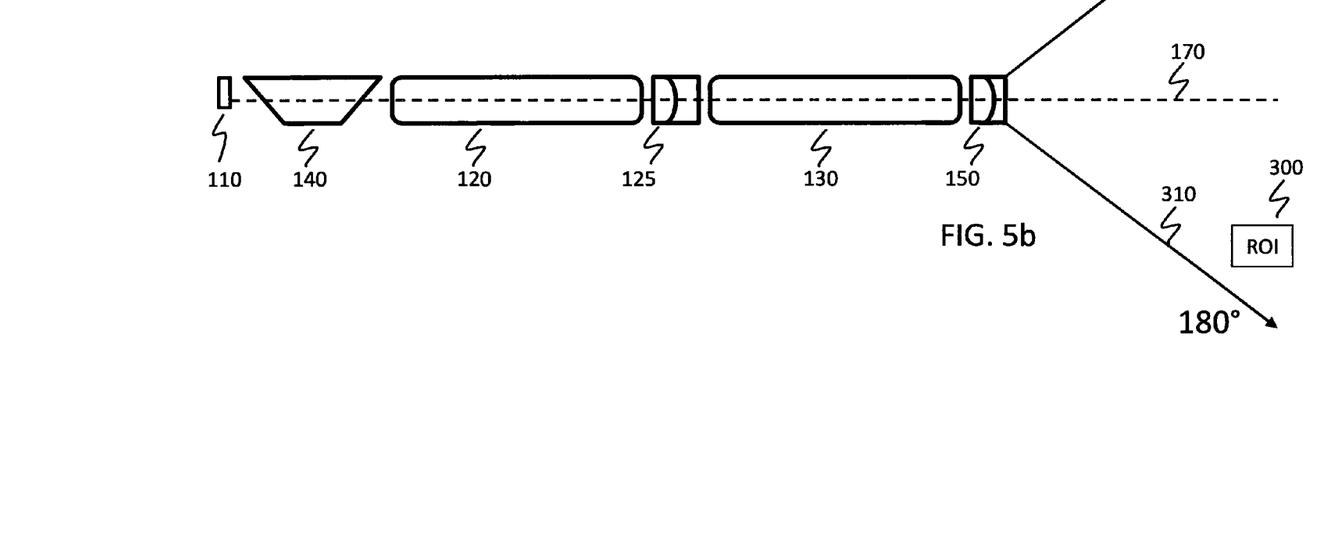
FIG. 5b depicts a rotated cross sectional side view of the endoscope of FIG. 3b where the optical rotator is rotated.

FIGS. 3-5 depict a region of interest ("ROI") 300 to be imaged by the endoscope 100. FIGS. 3a, 4a, and 5a depict a distal "on end" view of endoscope 100, and FIGS. 3b, 4b, and 5b depict a cross sectional side view of the endoscope 100. FIGS. 3b, 4b, and 5b all show the image sensor 110, optical rotator 140, relay lens system 120/125/130 and wide angle lens 150 in a linear fashion across wide optical axis 170.

As depicted in FIGS. 3a, 4a, and 5a, the image sensor 110 pixel array center-point may be offset from the longitudinal axis 170 of the endoscope 100. This enables the sensor view 110' to include the longitudinal axis 170, i.e. the offset of the image sensor 100 enables the 0° view vector of the endoscope 100 to always be included in the sensor view 110'. The wide viewing field 310 of the endoscope 100 is depicted by the larger, outer circle of FIGS. 3a, 4a, and 5a, and correspondingly depicted by the two solid arrows of FIGS. 3b, 4b, and 5b.

In certain embodiments, the optical rotator 140 may be a dove prism and may be rotated 400 to bring a ROI 300 into the sensor view 110', as depicted in FIG. 4a by arrow 410. In this manner, image sensor 110 may remain in a fixed and static position within the endoscope 100, while optical rotator 140 is rotated 400 to bring a ROI 300 into the sensor view 110'. The ROI 300 is now within the sensor view 110'; however, the ROI 300 is inverted 420. If desired, the user may revert or rotate 500 the ROI 300 via the image rotator. The image rotator may be a solid state/electronic image rotator for electronically rotating/changing the orientation of the sensor view 110'.

Figure 6:
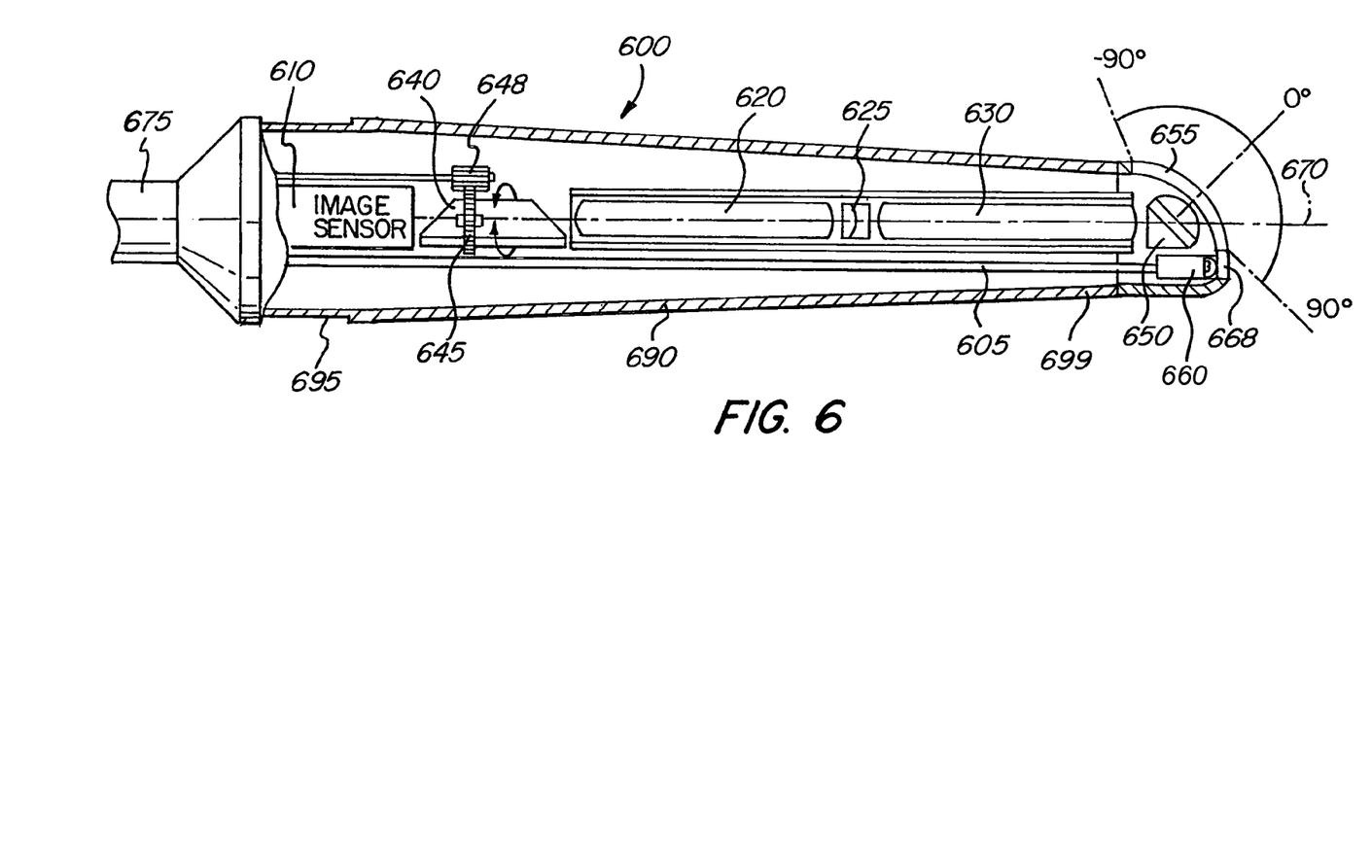
FIG. 6 is a side view of an endoscope of an embodiment of the invention where the body is tapered.

FIG. 6 depicts another exemplary endoscope 600 of an embodiment of the invention. Endoscope 600 has a body 690 with a wide angle lens 650 incorporated within the distal end of the body 690. Endoscope 600 has a longitudinal axis 670 extending from the proximal end to the distal end of the endoscope 600.

The body 690 is shown being tapered from proximal end 695 to distal end 699. The distal end 699 has a smaller diameter than proximal end 695. This allows an object of the invention to be realized, which is to keep the diameter of the endoscope at the distal end very small.

In FIG. 6, lens window 655 is shown at the distal end of the body 190. Lens window 655 is fully sealable. Endoscope 600 may be sterilized in an autoclave or other sterilization system.

Optical rotator 640 is also shown as a Dove-prism. Actuator 645 is shown being able to rotate the optical rotator. Controller 648 is shown being able to control the actuation of the actuator in accordance with an input signal from said input device. Actuator 645 is shown as a gear and controller 648 as an element that engages the gear. Other types of actuators and controllers may be used in various embodiments of the invention.

FIG. 6 also shows relay lens system 620/625/630. The relay lens system 620/625/630 may be made of singlets and doublets.

FIG. 6 also shows illumination system 660 disposed in the distal end of endoscope 600. Illumination system 660 may be composed of one or more light emitting diodes or other illumination elements known in the art. Wiring 605 provides power to illumination system 160. Lens window 668 is shown at the distal end of the body 690 and is fully sealable.

FIG. 6 also shows image sensor 610 incorporated in the proximal portion of endoscope 600. The proximal portion of the endoscope has a power cord 675 that provides power for the elements of the endoscope.

In certain embodiments, to even out the information density and improve the resolution of the imager, it is preferable that transmission system comprise an f-theta optical system or an f-sin(theta) optical system. An f-theta optical system uniformly separates the image rays incident to wide angle lens 150 by a distance proportional to f-theta, where f is the focal distance of the lens system and theta is the angle of incidence of the image rays relative to optical axis. The f-theta optical system provides a uniform distribution of the image field relative to the optical axis such that equivalent solid angles in the object will be imaged onto equivalently sized regions of the imaging area.

In an f-sin(theta) optical system the radial height of an image relative to the image location of the optical axis is proportional to the sine of the corresponding object angle from which it originated. An f-sin(theta) optical system provides a uniform f-number across the image plane, and therefore uniform illumination and potentially uniform MTF. Therefore image illumination and MTF (in the diffraction limit) will be uniform.

In certain embodiments, the image field gathered by wide angle lens system 150 is conveyed to the transmission system. The transmission system in turn conveys the wide angle field of view to an image sensor.

If the optical system does not correct the variation in information density attributable to the wide angle lens system, then it may be necessary to provide circuitry that can correct any distortion or uneven information density that can be present in the image signal or the region of interest signal. However, by utilizing an f-sin(theta) optical system, the need to incorporate corrective circuitry and the complexities associated with such manipulation can be avoided.

While the invention has been specifically described in connection with certain specific embodiments thereof, it is to be understood that this is by way of illustration and not of limitation, and that various changes and modifications in form and details may be made thereto, and the scope of the appended claims should be construed as broadly as the prior art will permit.

The description of the invention is merely exemplary in nature, and, thus, variations that do not depart from the gist of the invention are intended to be within the scope of the invention. Such variations are not to be regarded as a departure from the spirit and scope of the invention.

What is claimed is:

1. An endoscope comprising:
   a body having a distal end, a proximal end, and a longitudinal axis;
   a wide-angle objective-type lens disposed in the distal end of the body for capturing light of a wide viewing field;
   an image sensor having only one imaging surface disposed in the body for detecting the light captured by the wide-angle objective-type lens and forming one or more images of the wide viewing field;
   an optical rotator interposed between the wide-angle objective-type lens and the image sensor, the optical rotator being rotatable such that during a course of normal operation, any portion of the wide viewing field may be detected by the image sensor, the portion detected at any one time being a sensor view;
   a relay lens system interposed between the optical rotator and the wide-angle objective-type lens, the relay lens system transmitting the captured light of the wide viewing field to the image sensor for detection; and
   an actuator configured to rotate the optical rotator;
   wherein a center-point of the entire imaging surface is offset from an optical axis formed by the wide-angle objective-type lens, the relay lens system, and the optical rotator, the center-point being offset from the optical axis such that only some of the captured light of the wide viewing field is detected by the entire imaging surface and such that the sensor view includes the optical axis.

2. The endoscope of claim 1, wherein the wide-angle objective-type lens transmits the captured light of the wide viewing field for reception by the optical rotator, and
   wherein the optical rotator transmits the captured light of the wide viewing field to the image sensor for detection.

3. The endoscope of claim 1, wherein the optical axis is substantially parallel to the longitudinal axis of the body.

4. The endoscope of claim 3,
   wherein the wide-angle objective-type lens transmits the captured light of the wide viewing field to the relay lens system,
   wherein the relay lens system transmits the captured light of the wide viewing field to the optical rotator,
   wherein the optical rotator transmits the captured light of the wide viewing field to the image sensor for detection.

5. The endoscope of claim 1, further comprising an image rotator, wherein the image rotator rotates the orientation of the sensor view.

6. The endoscope of claim 5, wherein the image rotator is in communication with a processor for changing the orientation of the sensor view.

7. The endoscope of claim 6, wherein the image rotator changes the orientation of the sensor view in accordance with a user input or with a predetermined algorithm.

8. The endoscope of claim 6, wherein the processor changes the orientation of the sensor view in accordance with a user input or with a predetermined algorithm.

9. The endoscope of claim 1, wherein the wide-angle objective-type lens continuously captures the light of the wide viewing field.

10. The endoscope of claim 1, wherein the body includes a handle affixed to the proximal end of the body, and wherein the image sensor is disposed in the handle.

11. The endoscope of claim 1, further comprising an illumination system, wherein the illumination system provides light to at least a portion of the wide viewing field.

12. The endoscope of claim 1, wherein the image sensor continuously captures the light provided by the wide-angle objective-type lens.

13. The endoscope of claim 12, wherein the image sensor captures only a partial amount of the light provided by the wide-angle objective-type lens.

14. The endoscope of claim 1, wherein the actuator is selected from a group consisting of a hydraulic, mechanical, magnetic, electronic, or electrical actuator, and combinations thereof.

15. The endoscope of claim 1, wherein the body of the endoscope is tapered.

16. The endoscope of claim 1, wherein the relay lens system includes singlet and doublet lenses.

17. The endoscope of claim 1, wherein the optical rotator is a rotational prism selected from the group consisting of: Dove prisms, reversion or "K" prisms, delta prisms, and Pechan prisms.

18. The endoscope of claim 1, further comprising a controller for actuating the optical rotator, the controller configured to receive an input signal from an input device.

19. The endoscope of claim 18, wherein the input device allows for selecting a region of interest within the wide viewing field, wherein the region of interest is not larger than the sensor view.

20. The endoscope of claim 19, wherein the input device is selected from a group consisting of a knob, button, joystick, touchpad, touchscreen, foot pedal, gesture detection, voice control, and combinations thereof.

21. The endoscope of claim 20, further comprising an input facility, the input facility selected from a group consisting of a computer, a cloud computing module and a display.

22. The endoscope of claim 21, wherein the input facility involves moving the region of interest within the wide viewing field so as to select different portions of the wide viewing field for display.

23. The endoscope of claim 22, wherein the moving of the region of interest comprises calculations by a processor to relate the selected new position of the region of interest to the physical parameters of the mechanics of the endoscope.

24. The endoscope of claim 23, wherein the calculations comprise mathematical parameterization based on polar, Euclidean, or other appropriate coordinate systems.

25. The endoscope of claim 24, wherein the calculations comprise mathematical parameterization based on any coordinate system.

26. An endoscopic surgical system comprising:
an input device;
an endoscope having:
  a body having a longitudinal axis, a distal end, and a proximal end,
  a wide-angle objective-type lens disposed in the distal end of the body for capturing light of a wide viewing field,
  an image sensor having only one imaging surface disposed in the body for detecting the light captured by the wide-angle objective-type lens and forming one or more images of the wide viewing field,
  a relay lens system interposed between the wide-angle objective-type lens and an optical rotator, the relay lens system transmitting the captured light of the wide viewing field to the image sensor for detection,
  the optical rotator interposed between the relay lens system and the image sensor, wherein the optical rotator is rotated such that during a course of normal operation, any portion of the wide viewing field may be detected by the image sensor, the portion detected at any one time being a sensor view,
  an actuator configured to rotate the optical rotator,
  wherein a center-point of the entire imaging surface is offset from an optical axis formed by the wide-angle objective-type lens, the relay lens system, and the optical rotator, the center-point being offset from the optical axis such that only some of the captured light of the wide viewing field is detected by the entire imaging surface and such that the sensor view includes the optical axis;
a display for presenting to the user the selected portion of the sensor view corresponding to the region of interest in the wide viewing field;
wherein the input device allows a user to select a portion of the sensor view corresponding to a region of interest in the wide viewing field.

27. The endoscopic surgical system of claim 26, wherein the endoscope further comprises a solid-state image rotator.

28. The endoscopic surgical system of claim 27, wherein the solid-state image rotator is in communication with a processor, wherein the processor changes the orientation of the sensor view in accordance with a user input or with a predetermined algorithm.

29. The endoscopic surgical system of claim 26, wherein the input device is selected from a group consisting of a knob, button, joystick, touchpad, touchscreen, foot pedal, gesture detection, voice control, and combinations thereof.

30. The endoscopic surgical system of claim 26, wherein the body includes a handle affixed to the proximal end of the body, the image sensor being disposed in the handle.

31. The endoscopic surgical system of claim 26, further comprising an illumination system, wherein the illumination system provides light to at least a portion of the wide viewing field.

32. The endoscopic surgical system of claim 26, wherein the optical axis is substantially parallel to the longitudinal axis of the body.

33. The endoscopic surgical system of claim 26, wherein the image sensor continuously captures the light provided by the wide-angle objective-type lens.

34. The endoscopic surgical system of claim 33, wherein the image sensor captures only a partial amount of the light provided by the wide-angle objective-type lens.

35. The endoscopic surgical system of claim 26, wherein the optical rotator is a rotational prism selected from the group consisting of: Dove prisms, reversion or "K" prisms, delta prisms, and Pechan prisms.

36. The endoscopic surgical system of claim 26, wherein the endoscope further comprises a controller for actuating the optical rotator, the controller configured to receive an input signal from the input device.

37. An endoscope comprising:
a body having a longitudinal axis, a distal end, and a proximal end;
a wide-angle objective-type lens disposed in the distal end of the body, the wide-angle objective-type lens being able to collect light from a wide viewing field;
an illumination system for providing light to at least a portion of the wide viewing field;
an electronic image sensor having only one imaging surface disposed in the body;
an optical image transmission system interposed between the wide-angle objective type lens and the electronic image sensor, the optical image transmission system transmitting the captured light of the wide viewing field for detection by the electronic image sensor at any given time;
an optical rotator interposed between the wide-angle objective-type lens and the electronic image sensor for rotating the wide viewing field such that during a course of normal operation, any portion of the wide viewing field may be detected by the electronic image sensor, the portion detected at any one time being a sensor view; and
an actuator configured to rotate the optical rotator;
wherein a center-point of the entire imaging surface is offset from an optical axis formed by the wide-angle objective-type lens, the optical image transmission system, and the optical rotator, the center-point being offset from the optical axis such that only some of the captured light of the wide viewing field is detected by the entire imaging surface and such that the sensor view includes the optical axis.

38. The endoscope of claim 37, wherein the endoscope is configured to be coupled to a display and to an input device to form an endoscopic surgical system.

39. The endoscope of claim 37, wherein the optical image transmission system receives the light captured by the wide-angle objective-type lens,
wherein the captured light is received by the optical rotator,
wherein the optical rotator transmits the captured light of the wide viewing field to the electronic image sensor for detection at any given time, and
wherein the optical axis is substantially parallel to the longitudinal axis of the body.

40. The endoscope of claim 39, wherein the optical image transmission system includes lens that provides for f-sin (theta) distortion.

41. The endoscope of claim 37, wherein the optical image transmission system is a relay lens system or a coherent image fiber bundle.

42. The endoscope of claim 37, further comprising a solid-state image rotator for electronically rotating the orientation of the sensor view.

43. The endoscope of claim 42, wherein the solid-state image rotator is in communication with a processor, wherein the processor changes the orientation of the sensor view in accordance with a user input or with a predetermined algorithm.

44. The endoscope of claim 37, wherein the body has a diameter of less than 3 mm.

45. The endoscope of claim 37, wherein the body includes a handle affixed to the proximal end of the body, and wherein the image sensor is disposed in the handle.

46. The endoscope of claim 37, wherein the optical axis is substantially parallel to the longitudinal axis of the body.

47. The endoscope of claim 37, wherein the image sensor continuously captures the light provided by the wide-angle objective-type lens.

48. The endoscope of claim 47, wherein the image sensor captures only a partial amount of the light provided by the wide-angle objective-type lens.

49. The endoscope of claim 37, wherein the optical transmission system is an f-sin(theta) optical system.

50. The endoscope of claim 37, wherein the optical rotator is a rotational prism selected from the group consisting of: Dove prisms, reversion or "K" prisms, delta prisms, and Pechan prisms.

51. The endoscope of claim 37, further comprising a controller for actuating the optical rotator, the controller configured to receive an input signal from an input device.

52. The endoscope of claim 51, wherein the input device is selected from a group consisting of a knob, button, joystick, touchpad, touchscreen, foot pedal, gesture detection, voice control, and combinations thereof.

53. The endoscope of claim 52, further comprising an input facility, the input facility selected from a group consisting of a computer, a cloud computing module or a display.

54. The endoscope of claim 53, wherein the input facility involves moving the region of interest within the wide viewing field so as to select different portions of the wide viewing field for display.

* * * * *